United States Patent [19]

Hollar et al.

[11] Patent Number: 4,933,147
[45] Date of Patent: Jun. 12, 1990

[54] UNITIZED REAGENT CONTAINMENT SYSTEM FOR CLINICAL ANALYZER

[75] Inventors: Robert C. Hollar, Wildwood; Tung-Ming Huang, Elk Grove Village, both of Ill.

[73] Assignee: Abbott Laboratories, North Chicago, Ill.

[21] Appl. No.: 99,883

[22] Filed: Sep. 22, 1987

Related U.S. Application Data

[63] Continuation of Ser. No. 755,508, Jul. 15, 1985, abandoned.

[51] Int. Cl.$^5$ .............................................. G01N 35/02
[52] U.S. Cl. ...................................... 422/64; 422/102; 436/45
[58] Field of Search .................... 220/22.3, 23.8, 288, 220/293, 297, 315; 422/64, 72, 102; 436/45; 356/244, 246

[56] References Cited

U.S. PATENT DOCUMENTS

| | | | |
|---|---|---|---|
| 1,596,367 | 8/1926 | Miller | 220/293 |
| 1,700,503 | 1/1929 | Lyon et al. | 220/293 X |
| 1,775,318 | 9/1930 | Morgan | 220/293 X |
| 3,081,158 | 3/1963 | Winter | 422/64 |
| 3,276,615 | 10/1966 | De Pew | 220/293 X |
| 3,480,399 | 11/1969 | Hamilton | 422/102 |
| 3,497,320 | 2/1970 | Blackburn et al. | 422/102 |
| 3,582,285 | 6/1971 | Hamilton | 422/61 |
| 3,785,773 | 1/1974 | Rohrbaugh | 422/102 |
| 4,119,407 | 10/1978 | Goldstein et al. | 422/58 |
| 4,287,155 | 9/1981 | Tersteeg et al. | 422/64 |
| 4,298,570 | 11/1981 | Lillig et al. | 422/64 |
| 4,325,910 | 4/1982 | Jordan | 422/64 |
| 4,344,768 | 8/1982 | Parker et al. | 436/43 |
| 4,390,499 | 6/1983 | Curtis et al. | 422/64 |
| 4,456,581 | 6/1984 | Edelmann et al. | 422/72 |
| 4,515,889 | 5/1985 | Klose et al. | 436/45 |
| 4,518,076 | 5/1985 | Feisel et al. | 422/65 |
| 4,764,342 | 8/1988 | Kelln et al. | 422/72 |

FOREIGN PATENT DOCUMENTS

| | | |
|---|---|---|
| 1573100 | 8/1970 | Fed. Rep. of Germany . |
| 2533052 | 1/1977 | Fed. Rep. of Germany ...... 422/102 |
| 150648 | 5/1980 | Fed. Rep. of Germany . |
| 2940799 | 5/1980 | Fed. Rep. of Germany . |
| 2855651 | 6/1980 | Fed. Rep. of Germany . |
| 3134005 | 4/1982 | Fed. Rep. of Germany . |
| 3402304 | 7/1984 | Fed. Rep. of Germany . |

Primary Examiner—Robert J. Warden
Assistant Examiner—D. John Griffith, Jr.
Attorney, Agent, or Firm—Daniel W. Collins; Clifford A. Dean; Robert W. Stevenson

[57] ABSTRACT

Improvements in apparatus for performing an assay to determine the presence or amount of a substance in a test sample, which apparatus comprises means for dispensing one or more reagents from containment means therefor into a reaction vessel and means for dispensing the sample from a sample container into said vessel for reaction with the reagents during performance of the assay, are disclosed. The improvements reside in the apparatus further comprising containment means for the reagents integral and in combination with the sample container and the reaction vessel.

14 Claims, 5 Drawing Sheets

FIG. 6

UNITIZED REAGENT CONTAINMENT SYSTEM FOR CLINICAL ANALYZER

This application is a continuation of application Ser. No. 755,508, filed July 15, 1985 entitled "Unitized Reagent Containment System for Clinical Analyzer" by Robert C. Hollar, et al.

BACKGROUND OF THE INVENTION

The present invention is directed generally to automated or semi-automated liquid assay apparatus for conducting assays of various liquids, especially biological fluids, for substances contained therein. More specifically, the principles of this invention can be used especially advantageously as an improvement to apparatus such as the Abbott TDx ® Analyzer, to more advantageously perform diagnostic assays of such biological fluids, e.g., immunoassays and nephelometric assays.

The TDx ® Analyzer, commercially available from Abbott Laboratories, Abbott Park, Ill., is a well-known, automated instrument generally used to measure analyte concentrations in biological fluids such as serum, plasma and whole blood. The TDx ® system is designed for use by trained clinical laboratory technicians in hospital laboratories, in private laboratories and in physicians' offices.

The TDx ® Analyzer was originally designed to operate utilizing fluorescence polarization techniques. Fluorescence polarization techniques are based on the principle that a fluorescent labeled compound in solution, when excited by plane polarized light, will emit fluorescence having a degree of polarization related to its molecular rotational relaxation time. The molecular rotational relaxation time, and hence the magnitude of the fluorescence polarization response, is directly related to the molecular size of the compound. Accordingly, when plane polarized light is passed through a solution containing a relatively high molecular weight fluorescent compound, the degree of polarization of the emitted light will in general be greater than when plane polarized light is passed through a solution containing a low molecular weight fluorescent compound.

The fluorescence polarization principle is utilized in the TDx ® Analyzer by mixing a sample containing an analyte (or suspected of containing an analyte) with a "tracer,", i.e., a labelled compound similar to the analyte but capable of producing a fluorescence polarization response to plane polarized light. The analyte is generally a low molecular weight compound. Antibody specific to the analyte and the tracer is also included in the mixture. The tracer and the analyte compete for a limited number of receptor binding sites on the antibody. The amount of tracer that will bind is inversely related to the concentration of analyte in the sample, because the analyte and tracer each bind to the antibody in proportion to their respective concentrations.

The fluorescence polarization response of the solution to plane polarized light will give a quantitative indication of the relative amount of free and bound tracer, because of the discrepancy in molecular size between the former and the latter. The free tracer (i.e., the tracer in solution when not complexed to the antibody) is generally a relatively small molecule compared to the tracer-antibody complex, and will tend to exhibit a shorter rotational relaxation time, such that the incident plane polarized light becomes depolarized. In contrast, plane polarized light interacting with bound tracer will tend to remain highly polarized because the large antibody-tracer rotates very little between the time that light is absorbed and emitted.

Fluorescence polarization techniques usually are applied to analytes of relatively low molecular weight. Since the tracer employed must generally resemble the analyte in order to compete effectively for antibody receptor sites, the tracer itself, in such instances, will be relatively large and will tend to retain the polarization of plane polarized light. Accordingly, when this large tracer molecule is bound to the antibody, there will generally not be an appreciable difference in the fluorescence polarization response when compared with the response produced by the free tracer, so in such cases it may be necessary to consider alterative assay techniques, such as nephelometry.

Nephelometric techniques have been found to provide a means for measuring the light scattered from a solution containing large molecules or suspended particles. In accordance with these techniques, incident light is passed through a solution, a portion of the incident light is scattered, and then the amount of scattered light is measured. These techniques have application, for example, when immunoprecipitation assays are conducted. In such assays, antibodies are raised to the analyte, often forming large three-dimensional lattices. These lattices produce an increase in the light scattering properties of the solution.

The TDx ® Analyzer, for example, provides capabilities for both fluorescence polarization and nephelometric analysis, as well as for other systems of analysis. Whatever assay system is employed, in this Analyzer, as in various other instruments of the prior art, the assays have heretofore been carried out by well-known techniques which involve dispensing reagents from bulk containers located remotely from the test samples undergoing analysis, and mixing the reagents with the samples in reaction cuvettes while the latter are indexed, by means of a carrier comprising a rotating carousel or the like, from one analysis station to another. Although this methodology has proved to be generally satisfactory, it would be economical and useful, in terms of ease of analysis and speed, and advantageous in terms of reagent stability during storage prior to performance of the assays, to provide modification of the reagent and sample containment portions of such instruments which would enable substantially all of the reagents initially to be present in a single, sealed, self-contained device, in amounts which are appropriate for performing a singular, particular assay, and in close proximity to the test sample for ease of dispensing, rather than such reagents being dispensed by the instrument from bulk containers remotely located from the carrier for the samples. Accordingly, there exists a need for such modification and devices and assay methods which utilize such modifications, which would improve the performance of assays using such readily available analytical instrumentation.

SUMMARY AND OBJECTS OF THE INVENTION

The present invention comprises improvements in clinical analysis apparatus of the type aforedescribed, for adapting such apparatus for performing improved assays. The apparatus of the present invention is improved by modifying the reagent containment and sample carrier means (e.g., a rotating carousel) of the apparatus in order to enable more efficient assays to be performed therewith, with concomitant greater stability for reagents and the capability of easier and faster dispensing of reagents which are employed in such assays. The invention is based upon an improvement in apparatus for performing an assay to determine the presence or absence of a substance in a test sample. The apparatus comprises means for dispensing one or more reagents from containment means therefor into a reaction vessel and means for dispensing the sample from a sample container into said vessel for reaction with the reagents during performance of the assay. The improvement resides in the apparatus further comprising "unitized" containment means for the reagents. By "unitized" is meant that the reagent containment means is integral and in combination with the sample container and the reaction vessel.

Accordingly, a primary object of the present invention is to provide the foregoing modifications of these aspects of a clinical analyzer, to confer the advantages described herein.

A further object of the invention is to provide such modifications with minimal changes to the hardware or construction of the analyzer.

Still another object of the invention is to provide these modifications to an automated analyzer such that the analyzer will be able to perform improved automated fluorescence polarization, nephelometric (light scattering) and other assays.

Further objects and attendant advantages of the invention will be best understood by a study of the following detailed description of preferred embodiments together with the drawings.

DETAILED DESCRIPTION OF THE INVENTION

The present invention is directed to liquid analysis apparatus and instrumentation which is modified in accordance with the invention to provide the advantages hereinbefore described for assays performed with the apparatus, and for reagents used in such assays. Although the preferred embodiments of the invention described herein are specifically directed to adaptation of an automated analyzer, particularly the Abbott TD ® Analyzer, for this purpose, it is to be appreciated that the invention is not limited in its applicability to that particular instrument, but that the principles thereof can be applied to any conventional analyzer which one skilled in the art may desire to adapt for the improved performance of assays and to achieve the other advantages in accordance with the invention.

Turning now to FIGS. 1 through 4 of the drawings, the pre-existing Abbott TDx ® Analyzer is represented generally at 10, and the components thereof which are pertinent to the description of the preferred embodiments of this invention are also shown. Major features of the Analyzer 10 comprise an output printer 12; a bulk reagent container 14; a pipetter boom assembly 16; an output display 18; a carousel 20; a control panel 22; a lamp housing 24; a diluent and sample valve block 26; diluent and sample syringes 28; inlet tubing 30; a dilution buffer container 32 and interconnecting tubing 34. The TDx ® *System Operational Manual*, is available from the Diagnostics Divison of Abbott Laboratories and contains a more detailed description of the TDx ® Analyzer and its operation before the addition thereto of the improvements provided by the present invention.

The improvements of the present invention, such as applied to the Analyzer 10, relate particularly to physical modifications of and addition of unitized reagent containment means mounted upon the carousel 20. The unmodified carousel 20 is shown in some detail in FIGS. 2 through 4. As described in more detail infra, the principles of the invention provide advantageously the aforementioned unitized reagent containment means for use in the performance of assays utilizing the modified version of the carousel 20.

Although not an aspect of the present invention, a general description of the use and operation of the TDx ® Analyzer will now briefly be set forth. Referring to FIGS. 1 through 4 of the drawings, prior to the performance of a fully automated assay on the TDx ® Analyzer, an outer tray 36 of the unmodified carousel 20 is loaded with sample cartridges 38 which contain sample wells 40 and sample predilution wells 42, and an inner housing thereof 44 is loaded with reaction cuvettes 44a in which the sample and reagents are reacted, and the assay is carried out and read by the Analyzer. As is well known, the loaded carousel 20 is then placed in an analysis chamber of the Analyzer, as shown at 10 in FIG. 1, which is provided with a drive mechanism, such as a rack and pinion gear (not shown) for rotating the carousel 20 with respect thereto. The sample and the reagents are then pipetted by the pipetter boom assembly 16 into the reaction cuvettes 44a and the analysis is carried out. The reagents are conventionally pipetted from the bulk reagent container 14 (FIG. 1), which, as shown, is located remotely from the cartridges 38 and the cuvettes 44a.

Figure 1:
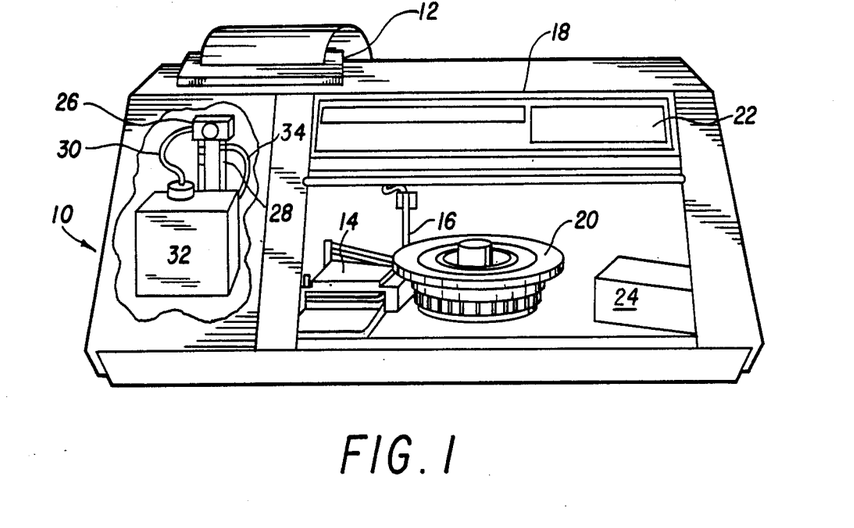
FIG. 1 is a perspective view of a prior art fluorescence polarization analyzer without the improvements provided by preferred embodiments of the present invention and showing the prior art sample and reaction vessel carrier ("carousel") and bulk reagent containment portions of the analyzer mounted therein.
Figures 2, 3:
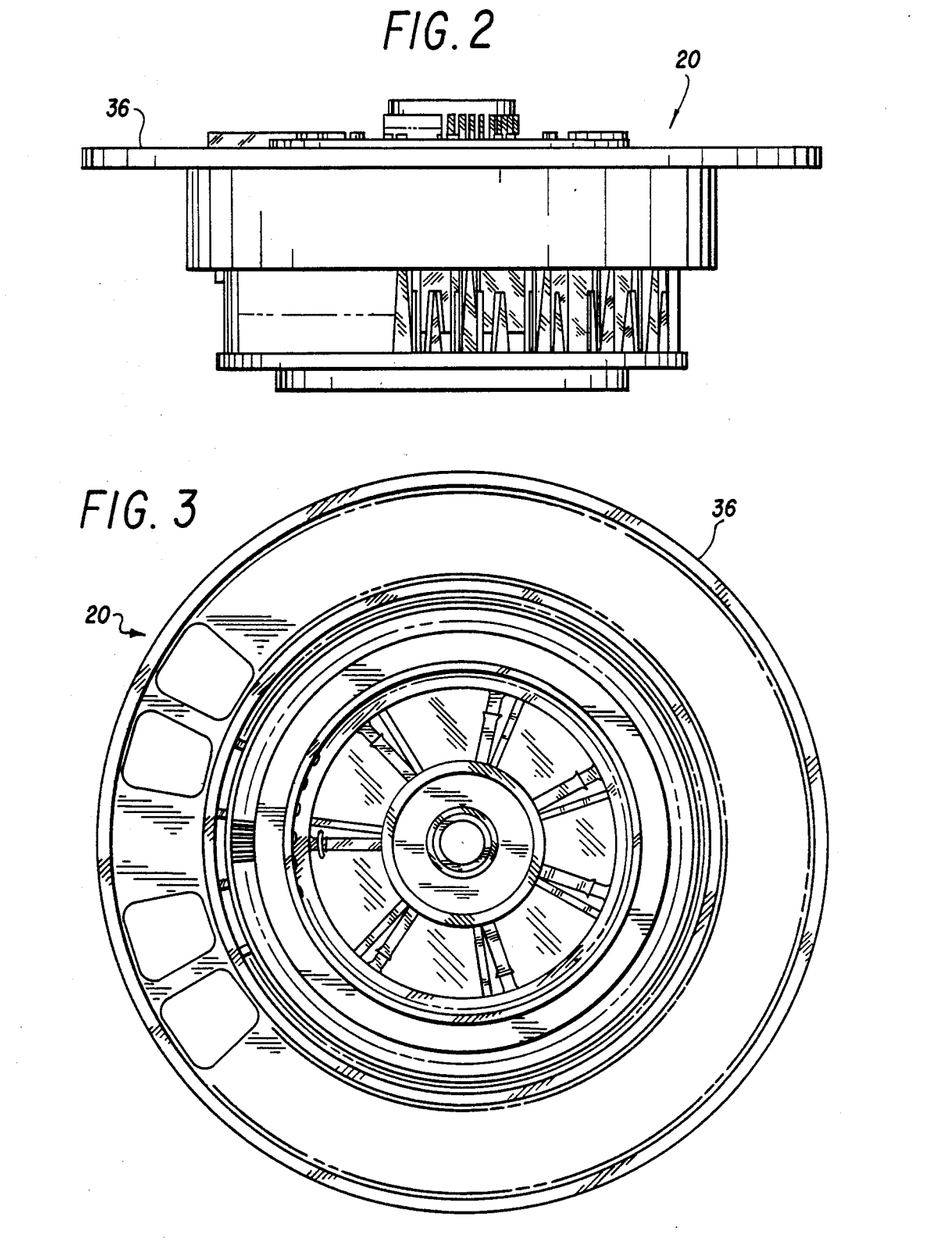
FIG. 2 is a side elevation view of the prior art carousel of FIG. 1.
FIG. 3 is a bottom view of the carousel of FIG. 2.
Figure 4:
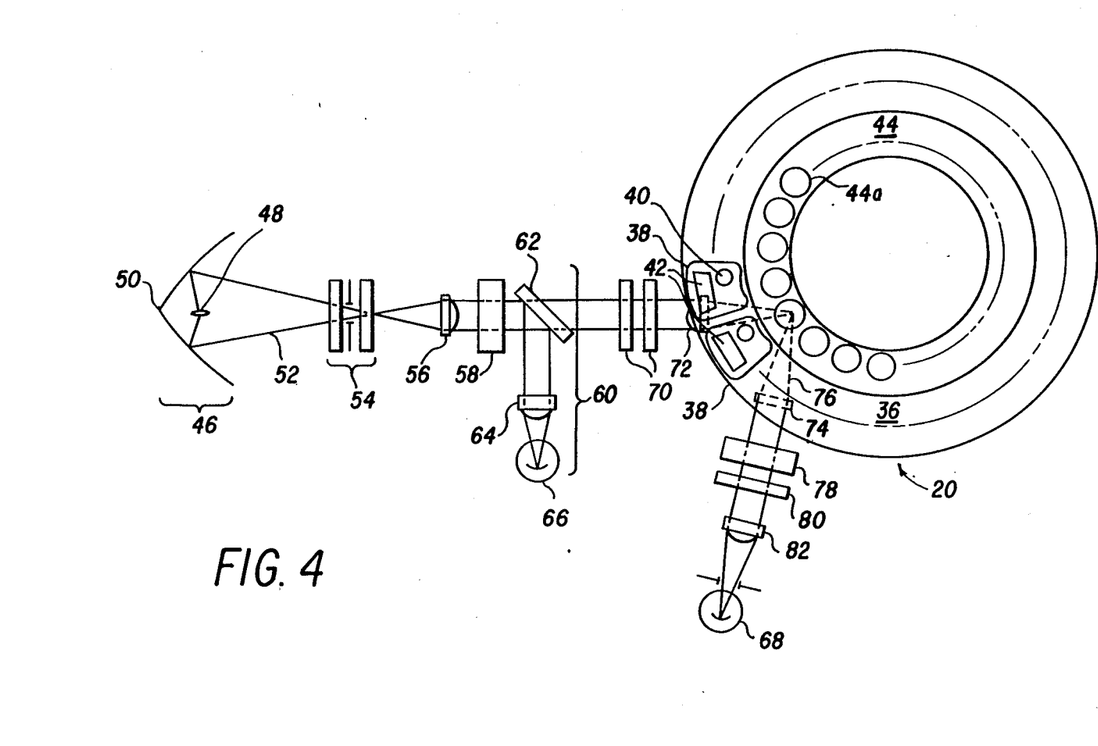
FIG. 4 is a schematic plan view of the carousel of FIG. 2 together with the associated fluorescence polarization optical system of the analyzer of FIG. 1.

A fluorescence polarization analysis using the Analyzer 10, for example, of FIG. 1, is conventionally conducted in accordance with the excitation and emission optics shown in FIG. 4. A lamp 46, comprising a tungsten filament 48 and a parabolic reflector 50, emits a beam of white light 52. The light beam 52 passes through an infrared absorbing lens 54, followed by an excitation collecting lens 56 and an excitation bandpass filter 58 centered, in a typical case, on a wavelength of about 485 nanometers. A reference assembly 60, comprising a reflector 62, a reference focusing lens 64 and a reference detector 66, diverts a portion of the beam 52 for monitoring the intensity of the beam 52 as the latter is emitted from the lamp 46. (In order to correct for variations in lamp intensity, the measurements are taken as a ratio of the signal from a photomultiplier detector 68 to the signal from the reference detector 66.) The remaining beam 52 passes to a liquid crystal polarizer 70 that alternately horizontally and vertically polarizes the light beam 52. Finally, an excitation condensing lens 72 focuses the light beam 52 on the center of one of the reaction cuvettes 44a, which, as is well known in the art of fluorescence polarization immunoassays, contains antiserum, tracer and sample.

The 485 nanometer light beam 52 excites fluorescein-containing compounds (i.e., bound and free tracer) contained in the reaction cuvette 44a, and these compounds respond by emitting light in a wavelength band ordinarily centered at approximately 525 nanometers. An emission collecting lens 74 captures the emitted light 76. This light 76 then passes through an emission bandpass filter 78, which permits light to pass through at about 525 nanometers. The light 76 then passes through a vertical polarizer 80, and an emission condensing lens 82 condenses the light 76, causing it to pass to the photomultiplier detector 68. The detector 68 detects the resultant signal and transmits current signals to associated, largely conventional electronics which interprets those signals as indicative of the presence and/or amount of an analyte in the sample.

As previously mentioned, the technique of fluorescence polarization, nephelometry and other methodologies for measuring the concentration of drugs or other analytes in biological fluids such as human serum or plasma, is well known. The present invention, although having broad applicability to various of these methodologies for testing of analytes in such fluids, and to both semi- or fully-automated assays, has been found to be especially advantageous when applied to improve such assays which are designed to be carried out on an analytical instrument such as the TDx ® Analyzer. Accordingly, for purposes of the present disclosure, the invention will be described, in its preferred embodiments, as applied to improve assays of the prior art which can be advantageously performed on a TDx ® Analyzer. A detailed description of the specific reagents and other substances which can be used in such improved assays made possible by the invention, and the procedures and techniques for performing such assays, are set forth in detail in U.S. Pat. No. 4,420,568, issued Dec. 13, 1983 and commonly assigned herewith, the disclosure of which patent is hereby incorporated herein by reference.

Figure 5:
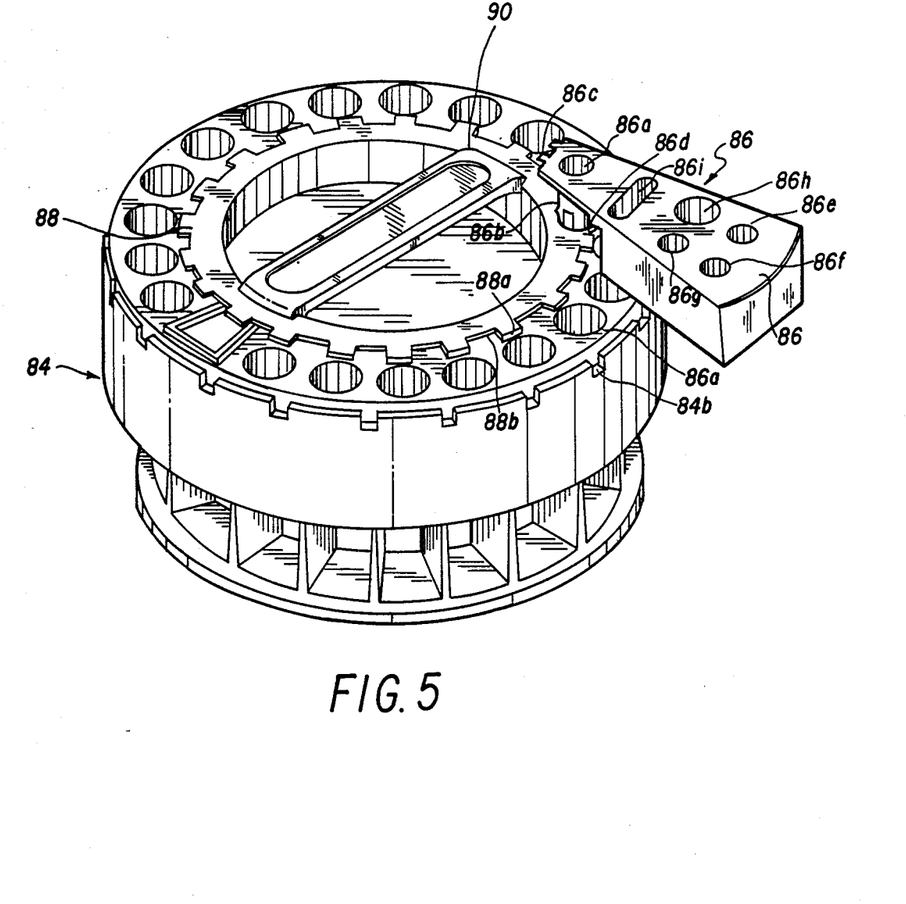
FIG. 5 is an perspective view of a carousel and unitized reagent containment means according to the present invention, which can be used in place of the prior art carousel and bulk reagent container shown in FIG. 1, to improve an analyzer such as that shown in FIG. 1.
Figure 6:
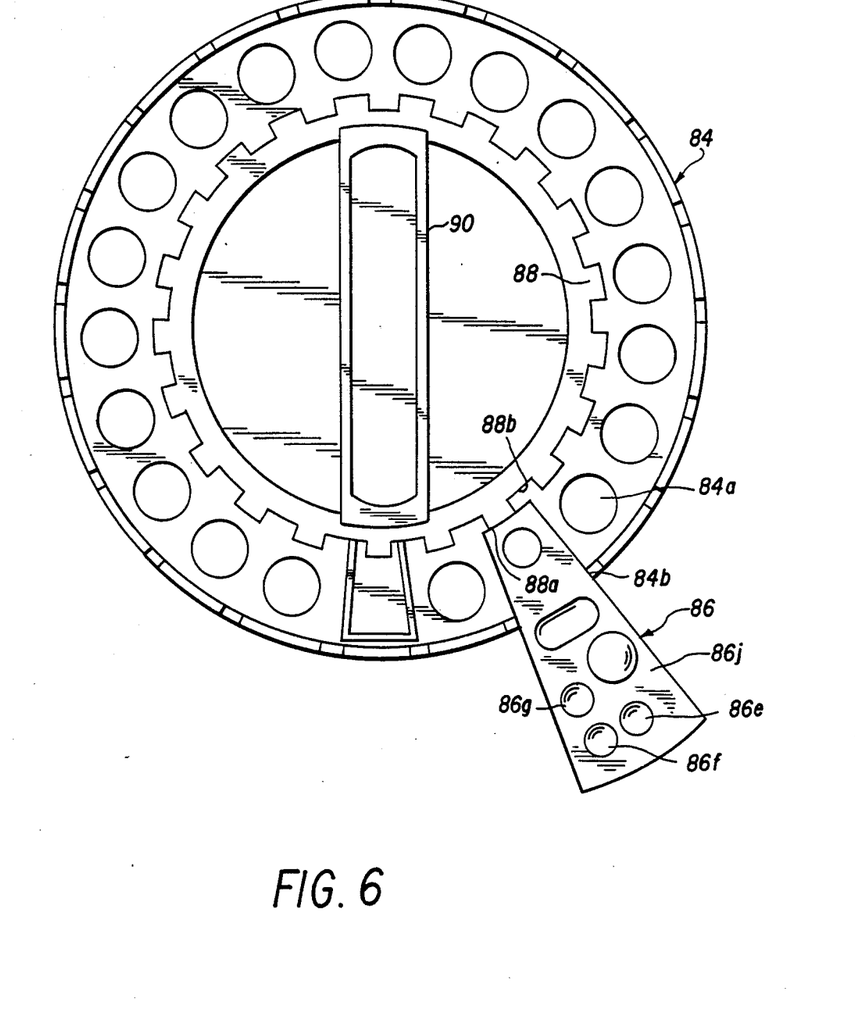
FIG. 6 is a top elevation view of the carousel and unitized reagent containment means of FIG. 5, showing these devices mounted together, as is the case during operation of the analyzer of FIG. 1 using these improvements provided by the present invention.
Figure 7:
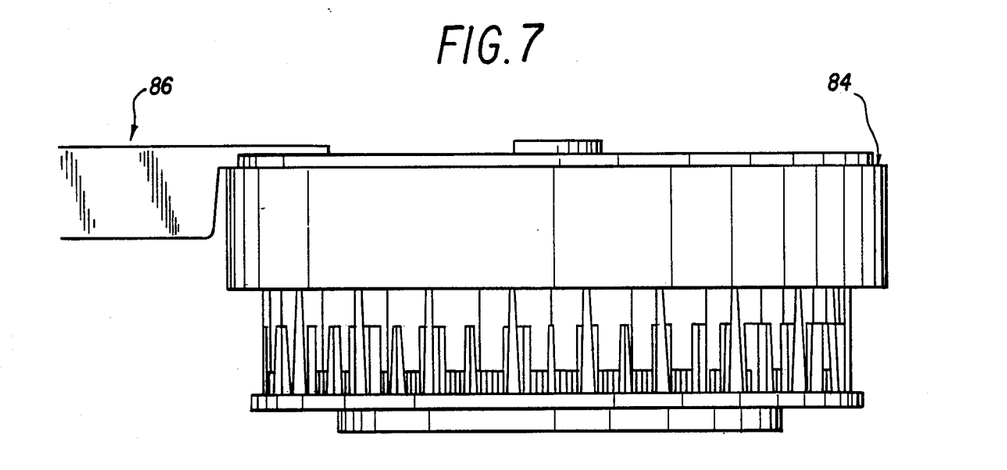
FIG. 7 is a side elevation view of the carousel and reagent containment means mounted together, as in FIG. 6.

FIGS. 5 through 7 illustrate a presently preferred embodiment of the present invention. In FIG. 5 is shown a modified carousel or tray 84 (in accordance with the invention) and unitized reagent containment means 86 in the form of a moulded structure (also in accordance with the invention). As is clearly illustrated in FIGS. 5 and 6 of the drawings filed in this continuation application, the rotatable carousel or tray 84 is characterized by a plurality of cuvette cavities 84a arranged in a circular pattern around the central axis of rotation thereof and the containment means 86 are each generally wedge or pie-shaped wherein the opposite sides thereof converge in one direction, or conversely, diverge in the opposite direction to provide a narrower portion and a wider portion. As shown, the carousel 84 and the containment means 86, prior to use thereof in the performance of an assay in an analyzer, are positioned by the operator of the analyzer such that a reaction cuvette holder 86a of the containment means 86, which has a depending slotted portion 86b, is above and in alignment with a corresponding cuvette cavity 84a of the carousel 84. Accordingly, when the carousel 84 and containment means 86 are placed in operation in the performance of an assay on the TDx ® Analyzer, means 86 fits securely upon the periphery of carousel 84, as best shown in FIGS. 6 and 7. It is to be appreciated that a plurality of containment means 86 can be so placed around the periphery of the carousel 84; any number of the means 86 so placed can contain reagents for different assays, or any number of means 86 so placed can contain reagents for the same assay, as desired by the operator of the analyzer.

Means 86 is mounted securely to the carousel 84 by the action of a locking ring 88, which locking ring 88 is co-axially and rotatably mounted on the carousel or tray 84 and spaced above the carousel or tray 84 a distance which is slightly greater than the vertical thickness of the inwardly projecting tabs or flanges 86c of the containment means 86. The locking ring 88, when rotated from an unlocked position to a locked position (e.g., by turning handle 90), moves locking flanges 88a of the ring 88 into position over corresponding flanges 86c of means 86, thereby to secure means 86 to the carousel 84. Thus, when ring 88 is in its unlocked position, recesses 88b therein are located over the flanges 86c of means 86, thereby enabling the latter to be removed from or placed into the carousel 84. It is also to be noted that in the preferred embodiment shown and described, a pair of circumferentially spaced notches 84b in the carousel 84 are adapted to engage corresponding depending flange portions or pairs of depending flanges 86d of each containment means 86 when each means 86 is placed into the carousel 84, thereby to further secure each means 86 thereupon against lateral movement and consequent instability.

The following description sets forth in greater detail the use of the aforedescribed preferred embodiments of the invention in the performance of a diagnostic assay. The specific details herein of construction and use of the preferred embodiments are intended only to disclose and to illustrate the invention, and are not to be construed as limitative thereof, any limitations being imposed only by the appended claims. For example, it will be appreciated by those skilled in the art that in addition to the particular configuration and arrangement of the individual reagent containment cavities of the unitized reagent containment means as described and shown, other configurations and arrangements can be conceived by those skilled in the art which will be fully within the concepts and teachings of this invention, and which will fully achieve the advantages of the invention. Furthermore, while the following detailed description involves primarily devices which are particularly suitable for an adapted to assays of human blood serum or plasma, it is apparent that one of ordinary skill in the art, given the teachings hereof, can apply the concepts of the invention to the assay of virtually any fluid, and in particular other biological fluids, such as whole blood, urine, spinal and amniotic fluid, and the like.

The use and operation of the TDx ® analyzer are well known; full details are, for example, set forth in the "TDx ® System Operation" manual, available from Abbott Laboratories, Abbott Park, Ill. The following description relates to the major functional aspects of the TDx ® Analyzer which are important to the concepts of the invention, to perform improved assays in accordance therewith. Accordingly, the following is to be read in conjunction with FIGS. 5 through 7 of the drawings.

Reagent/Sample Preparation (Typical Example)

Calibrators, Controls and a series of samples, e.g. human serum containing unknown levels of an analyte which it is desired to measure by means of the assay, are prepared. A centrifuge tube is designated for each sample to be tested, and placed in a suitable rack. A pipettor is filled with a precipitation reagent, designed to eliminate potentially interfering protein from the sample, and 200 microliters of the reagent are dispensed into each centrifuge tube. Then, 200 microliters of each serum sample are pipetted into its corresponding centrifuge tube containing the precipitation reagent. After pipetting of the samples, each centrifuge tube is capped and mixed on a vortex mixer for 3–5 seconds, to ensure thorough mixing. The tubes are then placed into a centrifuge head, and centrifuged for about ninety (90) seconds at 9,500 X g, until a clear supernatant and a hard compact pellet of denatured protein is obtained. After centrifugation is complete, each tube is uncapped and 250 microliters of the supernatant decanted into the corresponding sample well 86h of the reagent containment means 86, in preparation for performing the assay. The means 86 is then placed and locked into the carousel 84, as previously described, and the remainder of the assay procedure is performed as substantially a routine assay or calibration run would be performed on an unmodified TDx ® Analyzer, with the reagents for the assay being pipetted from the cavities 86e, 86f, or 86g, rather than from the bulk reagent container 14 (FIG. 1). In this regard, reference is made to the "Procedures for Operation" section of the "TDx ® System Operation" manual, previously described, for further details of the protocol used. The following is a description of the major aspects of the performance of the assay.

Assay Operation

All assay steps are controlled by the microprocessor and protocols programmed into the software of the TDx ® Analyzer. Preferably, a specific pattern on a barcode label on the means 86 is scanned by a barcode reader and the corresponding protocol for a particular assay is retrieved from the computer memory of the Analyzer. Each protocol contains detailed instructions for movement of pipetting syringes of the Analyzer which determines the volume of sample and the procedural steps for dispensing the reagents from their individual cavities in the means 86 in the pipetting steps, instructions for movement of a boom arm containing an aspirating probe, and instructions for movement of the rotating carousel 84 containing the reaction cuvettes. In addition, the protocol contains calibrator concentrations used for a calibration curve, in order to assure accuracy of the assay. The carousel 84 itself has unique identification means, such as a barcode, and a set of instructions in the protocol corresponds thereto which operate, e.g., stepper motors directed by an internal computer of the analyzer to move the carousel 84, and the syringes and boom arm relative thereto and to the means 86. A light beam focused on the carousel and controlled by the computer is used to monitor the number and placement of reaction cuvettes as the carousel rotates past the beam. Two electrodes attached near the end of the probe serve as a liquid level sensor which determines the presence of a liquid by electrical conductivity, thereby minimizing penetration of the probe into the samples and reagent cavities to aspirate or dispense.

During performance of an assay, the TDx ® Analyzer automatically pipettes reagents and test samples while simultaneously pipetting dilution buffer, then dispenses both into the reaction cuvette positioned in the holder 86a of the means 86 which has been placed into the carousel 84. Two pipetting syringes are driven down and the sample or reagent is aspirated at the same time the buffer is being drawn. When both syringes have been filled with the correct volumes, a boom arm moves the probe to the reaction cuvette, and the syringes are driven up, expelling their volumes. The liquids are probe is then moved vertically until the tip comes in contact with the liquid as the sample is aspirated. Upon completion of the aspiration, the boom moves up and horizontally, to position the probe over the dilution well or the cuvette. Coordinated rotation of the carousel occurs to bring a particular reaction cuvette into the correct position for receipt of dispensed liquid.

The dilution buffer rests on a platform (see FIG. 1) controlled by a microswitch which signals when the buffer is empty. Teflon tubing connects the buffer bottle to a valve block, liquid heater and boom arm. An integral valve directs the flow of liquids in and out of the syringe and tubing.

Some biological fluids, such as patient blood sera, evidence substantial background fluorescence which must be taken into consideration in order to obtain an accurate measurement of the analyte level in the sample. In the TDx ® Analyzer, a sample blank for each sample, calibrator or control is automatically made and read before a fluorescent tracer is added to the reaction mixture in each cuvette. To obtain an indication of the true background fluorescence present in the final sample, the mixture on the first reading must be at the final diluted concentration. This is accomplished by adding half the sample volume to a reaction mixture representing half the final reaction mixture. The blank mixtures are measured by the fluorescence detector and the intensities are stored in the computer memory of the instrument.

After the remaining reagents and the rest of the sample are added and incubated, the final reading is made. The blank intensities are subtracted from the final reaction mixture intensities before polarization values are automatically calculated by the computer of the TDx ® Analyzer. The polarization equation becomes as follows:

$$P = \frac{(I_{vv}\text{final} - I_{VV}\text{ blank}) - (I_{hv}\text{ final} - I_{hv}\text{ blank})}{(I_{vv}\text{final} - I_{vv}\text{ blank}) + (I_{hv}\text{ final} - I_{hv}\text{ blank})}$$

The net and blank intensity for each cuvette is also calculated and printed, using the equation $$I_{(\text{Net or Blk})} = 2\, I_{hv} + I_{vv}$$

As has been noted above, an important objective of the present invention is to modify the above-described prior art automated assay system (and other automated or semi-automated assay systems) so that assays can be conducted in accordance with the invention, without substantial alterations to the hardware of the analyzer.

The performance of an assay using a TDx ® Analyzer modified in accordance with the invention has been previously described. In performance of an assay on a TDx ® Analyzer which has been modified to perform assays in accordance with the improvements provided by the present invention, substantially the same procedures are followed as for conventional assays performed on an unmodified instrument, except that means 86 contains amounts of reagents, in cavities 86e, 86f and 86g (FIGS. 5 and 6) therein, which are only sufficient to perform *one* assay of a test sample in a reaction cuvette (not shown) which is placed in cuvette holder 86a thereof, rather than being dispensed from bulk containers. The sample well 86h and sample predilution well 86i of the means 86 are substantially the same as the corresponding wells 40 and 42 previously described of the sample cartridges 38 (FIG. 4), and, during performance of an assay, perform the same function. Thus, the modifications in assay procedure afforded by the present invention involve substantial improvements in pipetting of reagents from the cavities 86e, 86f and 86g during the various steps of the assay, by comparison with conventional pipetting of such reagents from the bulk reagent container 14 (FIG. 1). It will be apparent that modification of the carousel 20 in accordance with the invention can easily be accomplished to produce the carousel 84 of the invention as shown and described herein; thus, in performance of assays using the modified carousel 84, the carousel 84 performs substantially as has been described, and rather than being merely a sample carrier means, serves the function of indexing the means 86 which additionally contains reagents necessary to the assay.

As is apparent from the foregoing description, the combination of the modified carousel and the unitized reagent containment means provided by the invention, and the use of these, in combination, in liquid assay apparatus, provides the particular advantages of both enhanced reagent stability ("shelf-life"), because the reagents are present in a "unit-dose" format, and, because of the close proximity of the reagents to the sample and reaction vessel during the assay, enables more efficient, improved assays to be performed upon the apparatus. However, it is to be understood that the foregoing detailed description is to be considered as illustrative rather than limiting, since many variations within the scope of the invention which will fully achieve these and other advantages of the invention will be apparent to one of ordinary skill in the art. Accordingly, it is intended that the appended claims, including all equivalents thereof, be construed solely to define the scope of the invention.

What is claimed is:

1. A rotatable carousel for holding disposable containment means, each of which is characterized by a depending cylindrical cuvette holder, said carousel comprising:
   a plurality of cuvette cavities disposed in a circular pattern around a central axis of rotation thereof; and
   rotatable locking means disposed co-axially about said central axis and inwardly of said cuvette cavities, said locking means having a plurality of alternating notches and tabs around its periphery,
   whereby for insertion of a containment means comprising a depending cylindrical cuvette holder into said carousel, said locking means can be rotated so that said notches radially allign with one of said cuvette cavities to allow said containment means to be mounted on said carousel with its cuvette holder received in said one cuvette cavity, and upon so mounting said containment means, said containment means can be locked to said carousel by rotating said locking means so that one of said tabs radially aligns with said one cuvette cavity and overlies a portion of said containment means.

2. The carousel as recited in claim 1 wherein a plurality of upwardly opening notches are provided in the outer periphery of said carousel outwardly of said cuvette cavities and said rotatable locking means, said notches being adapted to receive a pair of flanges depending from a disposable reagent containment means when said containment means is mounted on said carousel.

3. A disposable reagent containment means for use in a carousel with multiple cuvettes and locking means rotatable between two positions, said containment means comprising:
   an inner portion adapted to overlay a portion of a carousel comprising multiple cuvettes and locking means rotatable between two positions, said inner portion having an opening and a downwardly depending cylindrical member adjacent said opening, said cylindrical member being adapted for supporting one of the cuvettes in the carousel;
   at least one locking projection extending from said inner portion, said locking projection being engagable by the rotatable locking means in one rotatable postion thereof;
   spaced depending flange portions projecting downwardly from said inner portion; and
   an outer portion having a plurality of recesses therein adapted to hold reagents or samples. an inner portion with a depending cylindrical member open at both its upper and lower ends and insertable in one of said cuvette cavities provided in said carousel tray, said cylindrical member being engageable with a cuvette, said containment means each having depending flange means disposed radially outwardly of said cylindrical member and adapted to be received in one of said plurality of peripheral notches provided in said carousel, and said containment means each having an outer portion provided with a plurality of open-topped recessed for holding reagents and a sample to be tested.

4. The containment means as recited in claim 3 wherein said cylindrical member is slotted at one end.

5. The containment means as recited in claim 3 wherein said outer portion includes a peripheral, downwardly depending flange.

6. The containment means as recited in claim 3 wherein said outer portion plurality of recesses define recesses for reagents, a sample recess, and a predilution well.

7. The containment means as recited in claim 3 wherein said containment means is wedge-shaped with said inner portion being narrower than said outer portion, whereby a plurality of said containment means can be assembled side-to-side in a circular pattern.

8. In combination, a rotatable carousel and a plurality of disposable reagent containment means removably mounted thereon, said carousel comprising a rotatable tray having a plurality of cuvette cavities disposed in a circular pattern around an axis of rotation thereof, and a plurality of upwardly opening notches provided in an outer periphery of said tray radially outwardly from said cuvette cavities, said disposable reagent containment means each having 9. The combination as recited in claim 8, wherein said carousel is provided with a generally circular locking member which is co-axially rotatable relative to said carousel tray ad which is spaced above said carousel tray a distance slightly greater than the vertical thickness of inwardly projecting tab means provided on said inner ends of said containments, the periphery of said locking member being provided with an alternating series of notches and locking tabs whereby, in one rotative position of said locking member, said notches thereon are aligned with said cuvette cavities to permit insertion of said cylindrical members of said containment means into said cavities with said flanges depending from said containment means being receivable in said peripheral notches on said carousel tray when said containment means are mounted on said carousel, and whereby, in a second angularly displaced rotative position of said locking member, said locking tabs thereon overlie said projecting tabs on said inner ends of said containment means whereby to lock said containment means on said carousel tray.

10. The combination as recited in claim 9, wherein a pair of said upwardly opening notches on the periphery of said carousel tray are provided for each one of said cuvette cavities, and wherein each containment means is provided with a pair of said depending flanges for engagement in a pair of said tray notches.

11. A carousel and reagent cassette for use in immunoassays, comprising:

a carousel having a plurality of cuvette cavities disposed in a circular pattern thereon;

a locking ring disposed inwardly of said cuvette cavities, said locking ring having a plurality of alternating notches and tabs, said locking ring being movable between a first position wherein said notches register with said cavities, and a second position wherein said tabs register with said cavities;

at least one cuvette inserted into one of said cuvette cavities; and at least one reagent cassette comprising a support member with a plurality of recesses for holding reagents and sample, a downwardly depending cylindrical member insertable into one of said cuvette cavities and engaging said cuvette, and tab means projecting inwardly of said carousel, said cassette being insertable into said carousel by moving said locking ring to the first position and placing said cylindrical member into said one cuvette cavity, said cassette tab means passing through a locking ring notch, said cassette being lockable into said carousel by moving said ring to said second position wherein a locking ring tab overlays said cassette tab.

12. The carousel and reagent cassette as recited in claim 11 wherein said carousel has a plurality of notches positioned radially outwardly of said cassette cavities, and said cassette has downwardly dependent flange means which engages at least one of said notches.

13. The carousel and reagent cassette as recited in claim 11 wherein said cassette is wedge-shaped.

14. The carousel and reagent cassette in claim 13 wherein said cylindrical member is slotted.

* * * * *